United States Patent
Chakravarthy et al.

(10) Patent No.: US 11,510,969 B2
(45) Date of Patent: Nov. 29, 2022

(54) WOUND TREATMENT CONTAINING COLLAGEN AND A GELATIN-REDUCING AGENT, AND METHOD FOR PROMOTING WOUND HEALING

(71) Applicant: Medline Industries, LP, Northfield, IL (US)

(72) Inventors: Debashish Chakravarthy, Vernon Hills, IL (US); Brian Mattorano, Chicago, IL (US); Anthony Frei, Glenview, IL (US)

(73) Assignee: MEDLINE INDUSTRIES, LP, Northfield, IL (US)

( * ) Notice: Subject to any disclaimer, the term of this patent is extended or adjusted under 35 U.S.C. 154(b) by 235 days.

(21) Appl. No.: 16/965,254

(22) PCT Filed: Nov. 16, 2018

(86) PCT No.: PCT/US2018/061562
§ 371 (c)(1),
(2) Date: Jul. 27, 2020

(87) PCT Pub. No.: WO2019/099860
PCT Pub. Date: May 23, 2019

(65) Prior Publication Data
US 2021/0060135 A1    Mar. 4, 2021

Related U.S. Application Data

(60) Provisional application No. 62/587,844, filed on Nov. 17, 2017.

(51) Int. Cl.
| | | |
|---|---|---|
| *A61K 9/14* | (2006.01) | |
| *A61K 38/39* | (2006.01) | |
| *A61L 26/00* | (2006.01) | |
| *A61K 9/70* | (2006.01) | |
| *A61K 47/34* | (2017.01) | |

(52) U.S. Cl.
CPC .............. *A61K 38/39* (2013.01); *A61K 9/146* (2013.01); *A61K 9/7007* (2013.01); *A61K 47/34* (2013.01); *A61L 26/0052* (2013.01); *A61L 2300/252* (2013.01); *A61L 2300/412* (2013.01); *A61L 2300/434* (2013.01); *A61L 2430/34* (2013.01)

(58) Field of Classification Search
CPC ........ A61K 9/146; A61K 38/39; A61K 47/42; A61L 26/0019; A61L 26/0033; A61L 26/0052; A61L 26/0095; A61L 2300/252; A61L 2300/412; A61L 2300/434; A61L 2430/34
See application file for complete search history.

(56) References Cited

U.S. PATENT DOCUMENTS

| | | | |
|---|---|---|---|
| 5,635,540 A * | 6/1997 | Edlich | A61K 9/0014 514/772.3 |
| 8,871,248 B2 | 10/2014 | Rodeheaver | |
| 9,283,278 B2 | 3/2016 | Rodeheaver | |
| 9,603,966 B2 | 3/2017 | Rodeheaver | |
| 2005/0079147 A1* | 4/2005 | Delaey | A61K 31/715 424/78.08 |
| 2013/0017227 A1 | 1/2013 | Lambert, Jr. | |
| 2014/0271471 A1* | 9/2014 | Sampath | A61L 27/54 424/1.85 |
| 2016/0324971 A1* | 11/2016 | Kilic | A61K 31/155 |

FOREIGN PATENT DOCUMENTS

| | | | |
|---|---|---|---|
| KR | 101101321 B1 | 1/2012 | |
| KR | 1020150128481 A | 11/2015 | |
| WO | 2010129547 A1 | 11/2010 | |
| WO | WO-2016054423 A1 * | 4/2016 | .......... A61K 31/726 |
| WO | 2017074093 A1 | 5/2017 | |

OTHER PUBLICATIONS

Choi et al. Development of Stabilized Growth Factor-Loaded Hyaluronate-Collagen Dressing (HCD) matrix for impaired wound healing. Biomaterials Research. 2016, vol. 20:9, pp. 1-7. (Year: 2016).*
Sigma-Aldrich, Product Specification, Pluronic F-68-solid. Downloaded May 19, 2022. (Year: 2022).*
Fleck et al., Puracol Plus, "Understanding the Mechanisms of Collagen Dressings," Advances In Skin & Wound Care, vol. 20 No. 5, dated May 2007 (pp. 256-259).
International Search Report and Written Opinion for International Patent Application No. PCT/US2018/061562 dated May 23, 2019.
Jeong et al., "Testing the influence of surfactant-based wound dressings on proteinase activity," International Wound Journal ISSN 1742-4801, dated 2016 (5 pages).
Medline Industries, Inc., PURACOL Collagen Wound Dressings, dated 2017 (8 pages).

* cited by examiner

*Primary Examiner* — Jeffrey E. Russel
(74) *Attorney, Agent, or Firm* — Fitch, Even, Tabin & Flannery LLP

(57) ABSTRACT

Disclosed is a wound treatment that includes collagen and a gelatin-reducing agent. Also disclosed is a wound dressing including a substrate, collagen, and a gelatin-reducing agent. The collagen and gelatin-reducing agent may be present in any suitable a weight ratio relative to one another, such as a weight ratio of about 0.25:1 to about 4:1 with respect to one another. Also disclosed is a method for promoting wound healing including administering collagen and a gelatin-reducing agent to a wound in need of treatment.

31 Claims, 2 Drawing Sheets

WOUND TREATMENT CONTAINING COLLAGEN AND A GELATIN-REDUCING AGENT, AND METHOD FOR PROMOTING WOUND HEALING

CROSS-REFERENCE TO RELATED APPLICATION

This application claims the benefit of U.S. Provisional Application No. 62/587,844, filed Nov. 17, 2017, which is incorporated herein by reference in its entirety.

FIELD

The application relates generally to a wound treatment and a method for promoting wound healing, particularly chronic wounds.

BACKGROUND

After an injury, including accidental or medically-induced injuries to the skin or other affected tissue, the body undergoes a natural process to repair the damage. The wound repair process involves a complex coordination of biochemical processes to remove damaged cells and tissue and to promote new tissue growth. Many wounds heal quickly with minimal medical attention. For severe acute wounds, the healing process may be delayed and may result in painful inflammation, infection, or scarring. Significant medical attention may be required for such wounds. Additionally, chronic wounds, such as pressure sores, diabetic foot ulcers, and arterial ulcers, generally require significant medical attention. A variety of medical conditions may also complicate and slow the healing process, including diabetes or diseases that cause poor blood circulation. In such cases, additional steps are desirably taken to assist the natural wound healing process.

During the normal wound repair process, fibroblasts produce collagen, which is a structural protein that plays an important role in new tissue development. Fibroblasts are recruited to the wound site and collagen expression is upregulated. In some wounds, such as chronic wounds, a failure or delay in fibroblast recruitment or collagen expression at the wound site can adversely affect wound healing. Chronic wounds may also be characterized by high matrix metalloprotease ("MMP") levels. MMPs comprise a family of enzymes involved in the breakdown of the extracellular matrix. Of these, collagenases generally degrade intact collagen, while gelatinases generally degrade denatured or damaged collagen (i.e., gelatin). Necrotic tissue contains a high proportion of damaged collagen. Living tissue contains a higher proportion of non-degraded collagen. In general, intact collagen is a precursor of degraded gelatin.

MMPs generally play a helpful role in the early, inflammatory phase of wound healing when they are essential to clean up loose, unanchored collagen (that role is played by collagenase MMPs) as well as degraded collagen (that degradation or clean up role is played by the gelatinase type of MMPs). However, excessive MMP levels or higher levels of some MMPs versus others, long after the acute inflammatory phase should have passed, can inhibit the wound healing process by resulting in ineffectually low collagen levels at the wound site. MMP levels are affected, at least in part, by levels of other enzymes, such as elastase, which converts MMP precursors to active MMPs. Accordingly, high elastase levels in the wounds also promote faster collagen breakdown and lower collagen levels at the wound site. Elastases also break down a key protein elastin.

A major direct, as well as indirect, source of MMPs and other proteinases are wound pathogens in necrotic tissue. High levels of proteases result from a combination of related factors. First, the microbes themselves secrete the degradative and inflammatory enzymes to catabolize tissue and tissue associated substances (e.g., extracellular matrix or "ECM" that contain collagen and gelatin) to provide nutrition for themselves. Second, the high levels of bacteria associated with necrotic tissue recruit cells of the innate immune system that secrete these proteinases on a continuous basis. In the delay of wound healing for chronic wounds, the presence of necrotic tissue is a significant cause of these problems, and it is difficult to remove all of the necrotic tissue using a surgical or other mechanical technique.

It has been reported that bacterial biofilms are associated with a significant percentage of chronic wounds. The microbes associated with biofilms are a significant source of MMP levels in chronic wounds. The biofilms become tolerant to antibiotic therapy and are difficult to eliminate. Studies have shown that surgical debridement can temporarily remove biofilms but that biofilms can return within days. The presence of biofilms leads to massive congregation of macrophages which are unable to physically penetrate the exopolymeric matrix and simply remain persistent in the wound site and secrete inflammatory enzymes such as MMPs, which include collagenases and gelatinases. The former delays wound healing.

It also has been reported that tissue inhibitors of metalloproteinases ("TIMPs") levels are generally slightly lower in chronic wounds than in acute wounds. Unchecked, MMPs can also result in the unwanted destruction of beneficial proteins, such as growth factors, growth factor receptors, and TIMPs, that are important for the healing process.

It is therefore generally desired to provide a composition and method that is effective to increase collagen levels while reducing gelatin at the wound site, thereby promoting wound healing. It has been found that a wound treatment can comprise, in combination, collagen and a gelatin-reducing agent. Preferably, at least a majority of the collagen is native collagen, and the gelatin-reducing agent is a poloxamer. The wound treatment may take any suitable form, such as a wound dressing. It is believed that collagen will interact with collagenases naturally present in the wound to preserve the collagen, thus inhibiting gelatin formation, and that the poloxamer or other gelatin-reducing agent will both help to physically remove gelatin from the wound and to inhibit gelatin formation by one or more actions of potentiating gelatinases or depotentiating collagenases in the wound.

DETAILED DESCRIPTION

Figure 1:
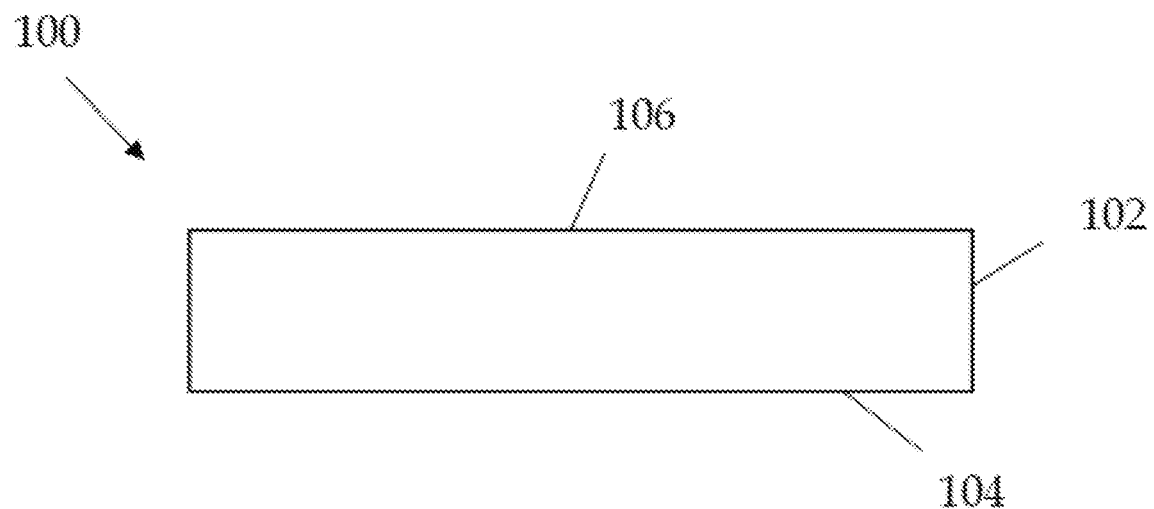
FIG. 1 is a side view of a wound treatment dressing according to one embodiment.

Provided herein is a wound treatment comprising a gelatin-reducing agent and collagen. A method of promoting wound healing is also provided. As described in more detail below, the wound treatment may be applied directly to the wound, applied to a bandage or dressing that covers the wound, or re-suspended in solution and injected into the wound or its penumbra to promote wound healing. The treatment is believed to result in improved wound healing, which potentially can result in reduced pain, less scarring, and/or avoidance of other more invasive treatments, such as skin grafting. The wound treatment provided herein also advantageously addresses the problem of necrotic tissue removal and promotes healing via the unique combination of collagen and gelatin-reducing agent.

The wound treatment may be administered to a variety of wounds, including wounds on the surface of the skin or internal wounds. Generally, the term "wound" includes any tissue or organ damaging or penetrating injury, such as a cut, puncture, biopsy, bite wound, abrasion, contusion, laceration, incision or other surgical wound, or wound resulting from a firearm or explosive device. The term "wound" also includes thermal wounds (such as frostbite, sunburn, radiation, or burn caused by fire, intense heat, steam, or hot liquid) and chemical wounds (such as from contact with a caustic chemical). Chronic wounds include, for example, pressure sores, diabetic foot ulcers, and arterial ulcers.

Generally, the wound treatment comprises collagen and a gelatin-reducing agent. The term "gelatin-reducing agent" as used herein refers to agents useful in the wound treatments described herein, which are effective to reduce the amount of gelatin, and in some cases eliminate the amount of gelatin, physically present at the wound site. The gelatin-reducing agent is a separate ingredient from the collagen or collagen derivative used herein. In other words, for purposes herein, the collagen or collagen derivative is not considered the gelatin-reducing agent, and a second ingredient in the wound treatment is used to fulfill the role of the gelatin-reducing agent. The gelatin-reducing agent may act by deactivating, sequestering, or otherwise reducing the activity of collagenase at the wound site, and/or to increase or otherwise upregulate gelatinase activity in the wound. The gelatin-reducing agent may also assist in physically removing gelatin from the wound site. Each activity individually has the effect of reducing the amount of gelatin physically present and/or formed in the wound. In at least one approach, the gelatin-reducing agent is effective to both decrease collagenase activity and increase gelatinase activity. By reducing or otherwise suppressing collagenase activity, which has little redeeming value in chronic wounds, and increasing gelatinase activity, which functions to remove necrotic tissue that itself delays wound healing (e.g., via the cycle of promoting bacterial growth, biofilm formation, immune cell ingress and persistence, and chronicity), the net result is protection of intact tissue and elimination of degraded necrotic tissue at the wound site.

It is believed that, as a general matter, collagen is desirable in the wound healing process. The natural healing process causes collagenases to be generated in the region of a wound, and the collagenases cause the formation of necrotic tissue, which is principally gelatin or hydrolyzed collagen. It is further believed that gelatinases cause degradation of the gelatin into small molecules, which exit the wound via natural biological processes. The introduction of collagen from an external source is believed to biologically interact with collagenases in the wound to inhibit hydrolysis of natural collagen produced in the wound. Patients with comorbidities, such as diabetes, tend to have more difficulty generating natural collagen at the wound site. Therefore, there is a significant need to preserve the natural collagen produced in a patient who may be generally unwell with comorbid conditions. The collagen in the wound treatment may act as a sacrificial substrate for collagenases in the wound. Introduced collagen in some cases may also cause some non-catalytic binding of collagenases in the wound, thereby further making the collagenases less bioavailable for activity in the wound.

The collagen in the wound treatment may be provided in a variety of forms, including native collagen ("Type 1") or denatured collagen (i.e., collagen that has lost its triple helical structure). It is preferable, however, that at least a majority of the collagen (in another aspect at least about 60 percent, and in another aspect at least about 75 percent of the collagen) should be present as native collagen, i.e., collagen that has not been denatured. The collagen may be derived from a variety of sources, including, for example, human (e.g., placental collagen), bovine, porcine, equine, or avian sources. In particular, a non-antigenic purified form of collagen may be used. Commercially available forms of collagen include, for example, PURACOL Plus Ultra (Medline, Inc.), which has native collagen structure. This has the effect of reducing the amount of collagenase available to degrade collagen produced in the wound site, thereby stabilizing or increasing beneficial collagen levels in the wound. In doing so, gelatin formation, and in turn de novo necrotic tissue formation, is advantageously reduced.

Any suitable gelatin-reducing agent may be employed. One particularly preferred gelatin-reducing agent is a surfactant, by which is contemplated a substance capable of reducing the surface tension of a liquid. In one particular approach, the gelatin-reducing agent is effective to remove slough and necrotic tissue. Because degraded collagen or gelatin may be loosely adherent to the wound bed, a biocompatible non-ionic surfactant capable of forming micelles may be used to sequester gelatin or gelatinous necrotic tissue and physically remove it from the wound. Suitable surfactants include, for example, glycolipids, phospholipids, ethoxy laces (such as poloxamers), poloxamines, and fatty acid esters such as glycerol monolaurate or Tweens. In some embodiments, the gelatin-reducing agent comprises or is a poloxamer. Various poloxamers are commercially available, such as a poloxamer 101, poloxamer 105, poloxamer 105 benzoate, poloxamer 108, poloxamer 122, poloxamer 123, poloxamer 124, poloxamer 181, poloxamer 182, poloxamer 182 dibenzoate, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403 and poloxamer 407, or a combination thereof. In one particular approach, the poloxamer comprises or is poloxamer 188. Poloxamers are named with a three-digit number, where the first two digits multiplied by 100 indicate the molecular mass and the last digit multiplied by 10 indicates the polyoxyethylene content. Commercially available PLURONIC® poloxamers may be obtained from Sigma-Aldrich or BASF Corporation. Poloxamer 188 is provided in the product PluroGel (available from Medline Industries). Poloxamer 188 is also sold in powder or granular form as Kolliphor® P 188 Micro (BASF). As noted above, microbes associated with biofilms are a significant source of MMP levels in chronic wounds. Therefore, particularly preferred gelatin-reducing agents for the wound treatment compositions and methods described herein, such as poloxamer 188, are also effective to remove biofilms. Gelatin formation is indirectly reduced when biofilms are broken up and removed by the surfactant. Accordingly, particularly preferred surfactants are effective to physically remove necrotic tissue (e.g., via micelle carriers), suppress collagenase activity, amplify gelatinase activity, and degrade and remove biofilms.

Advantageously, the gelatin-reducing agents useful herein do not degrade the collagen included in the treatment. Therefore, the activity of the collagen to suppress MMP activity can act in parallel with that of the gelatin-reducing agent. Also, the gelatin-reducing agents useful herein are not deactivated by common wound healing agents, such as antimicrobial silver ions.

The wound treatment may be provided in a variety of forms, such as in a powder, gel, paste, cream, foam, wash, or other liquid form. The wound treatment may also be formed into a film-like substrate. Liquid formulations of the wound treatment can be prepared, such as, for example, in the form of a solution or suspension in a non-toxic, parenterally-acceptable solvent or diluent. In another approach, the formulation may be a powder or lyophilizate that is reconstituted in a liquid or other media of choice prior to use. In yet another approach, the wound treatment may be in the form of an emulsion or liquid concentrate for dilution prior to administration. Exemplary pharmaceutically-acceptable carriers include saline, PEG, phosphate buffered saline, isotonic saline, Ringer's solution, dextrose, sterile water, deionized water, glycerol, ethanol, 5% dextrose in water, or other biocompatible liquid, and combinations thereof. For example, the wound treatment may be administered to the wound as a component of a bioadhesive.

The wound treatment may also further comprise one or more additional pharmaceutically acceptable components, such as to provide a desired viscosity or tackiness to the composition. The wound treatment may further include additional active agents, such as an antibiotic, antimicrobial (e.g., silver- or iodine-containing compounds), provitamin, antioxidant, vitamin, moisturizer, scar reducing agent, or other active agent known to promote wound healing. In one particular approach, the wound treatment further comprises iodine.

The wound treatment can be stored, such as in sealed vials or ampules, for long periods of time and used on an as needed basis. Powdered or other "neat" wound treatments provide great flexibility to the applications in which they may be used. For example, the composition in powdered or granular form may be used upon hydration, reconstitution, or suspension in liquid or other media before administration to a subject. The mixture may also be sterilized before being administered to the subject. The wound treatment can also be administered to a subject in powder or granular form and without reconstitution.

In one particular approach, the gelatin-reducing agent and collagen or collagen derivative are provided in granular/powdered form and mixed together. In one approach, the collagen or collagen derivative may act as a vehicle for delivery of the gelatin-reducing agent. Pharmaceutically-acceptable solid excipients may also be included. The mixed powder is filled in vials. An appropriate quantity of fluid, such as water, saline, or PEG, may be added to the vial and then the mixture can be poured or dispensed via syringe into the wound to be treated.

The collagen and the gelatin-reducing agent may be present in any suitable amounts relative to one another. For example, the wound treatment may include collagen and gelatin-reducing agent in a weight ratio of about 0.25:1 to about 4:1, or a ratio of about 0.5:1 to about 2:1, or the ratio may range from 35:65 to 65:35, or may be about 1:1.

The wound treatment may take the form of a wound dressing that comprises the collagen and gelatin-reducing agent on a substrate. In one embodiment, and as shown in FIG. 1, where the wound treatment is applied to a substrate to form a wound dressing, dressing 100 comprises at least one layer 102 and has a wound contacting surface 104 that would be positioned adjacent the wound during wound treatment. The wound treatment may be extruded, sprayed, sprinkled, laminated, or otherwise applied onto the layer 102. The wound treatment may be applied to the wound contacting surface 104 or non-wound contacting surface 106. The substrate may be of cotton, nonwoven synthetic material, or any suitable substrate material. Generally, the collagen should be present in the wound dressing in an amount effective to reduce or inhibit wound collagenase activity, and the gelatin-reducing agent should be present in an amount effective to reduce or mitigate wound gelatin formation. In one approach, the wound dressing may include up to about 5 grams of collagen and up to about 5 grams of gelatin-reducing agent per 100 square centimeters of surface area.

Figure 2:
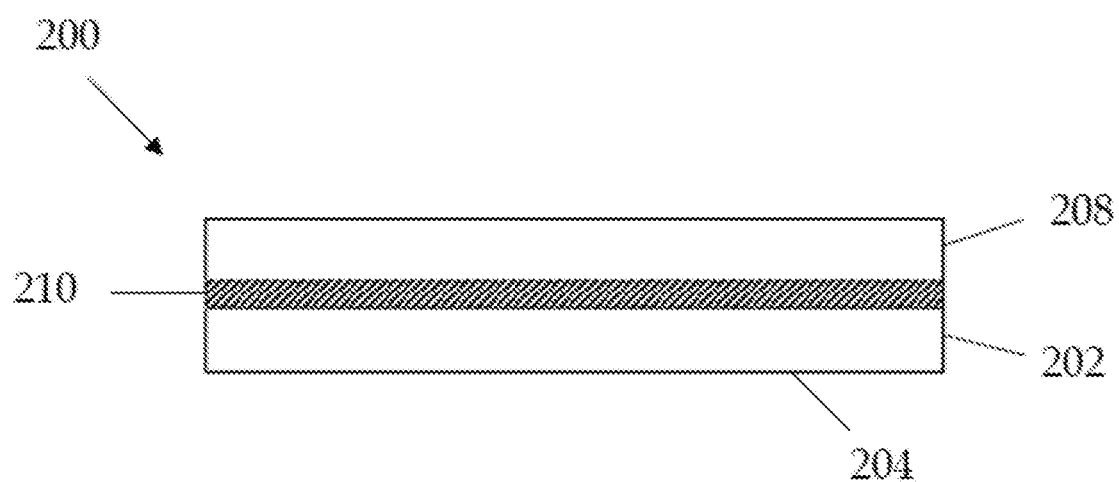
FIG. 2 is a side view of an alternative wound treatment dressing.

In another embodiment and as shown in FIG. 2, dressing 200 comprises at least two layers. Layer 202 is a wound contacting layer and has a wound contacting surface 204. The dressing 200 further comprises layer 208. The wound treatment may be applied to wound contacting layer 202 or layer 208. Optionally, there may be an adhesive layer 210 positioned between layer 202 and layer 208. The wound treatment may also be present in a separate layer positioned between layer 202 and layer 208 in addition to or instead of layer 210.

Figure 3:
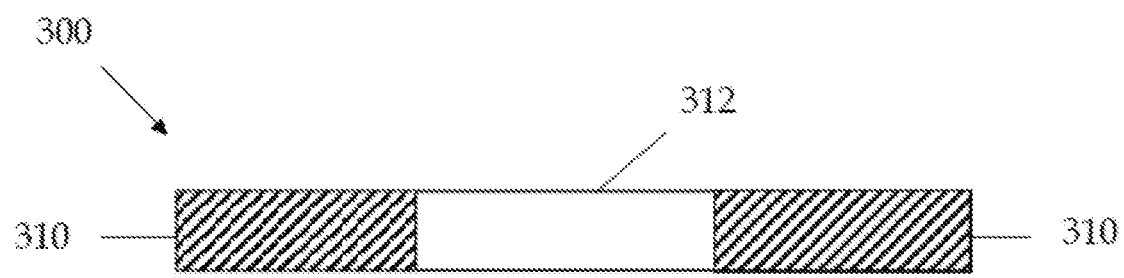
FIG. 3 is a side view of yet another alternative wound treatment dressing.

In yet another approach and as shown in FIG. 3, the dressing 300 may comprise at least one adhesive portion 310 and a wound contacting portion 312 (such as in the format of a bandage with two adhesive portions separated by a wound contacting portion). The wound contacting portion 312 may comprise any of the configurations described herein, such as in dressing 100 or 200.

One or more of the layers of the dressing may include pores or other openings effective to allow moisture or other bodily fluid to pass from the wound to the wound treatment present in or on the dressing. One or more of the layers may also have a minimum or maximum moisture vapor transmission rate, if desired. Any of the configurations described herein may further comprise a non-absorbent layer, such as a top layer, that does not contact the wound and is moisture resistant or impervious so as to contain any blood or other exudate from the wound. The one or more layers of the dressing may include, for example, a polymer film, polyurethane foam, cellulose fiber, nonwoven fabric, woven fabric, paper, adhesive, or any combination thereof. The one or more layers may also include one or more additional active agents that have been applied thereto.

The dressings provided herein may also be provided in a variety of forms, such as in the form of a sheet, patch, bandage pad, roll, or the like. In this respect, the dressing may be in the form of an individual unit or as a larger unit that may be subdivided to provide smaller dressings, as needed. At least in some approaches, the dressing is flexible to permit the dressing to conform to the shape of the wound site.

Also provided herein is a kit comprising collagen and a gelatin-reducing agent. For example, the collagen and gelatin-reducing agent may be provided in powder form. The kit may further include liquid media for reconstituting, hydrating, or otherwise suspending the powdered collagen and gelatin-reducing agent. The kit may also include instructions for mixing the collagen and gelatin-reducing agent in the media to form a wound treatment and for applying the wound treatment to a wound. If desired, the kit may further comprise bandages or other dressings.

Methods are also provided for promoting wound treatment comprising administering a therapeutically effective amount of collagen and a gelatin-reducing agent to a wound of a subject. Promoting wound healing comprises, for example, accelerating wound closure. Promoting wound healing may also comprise removal of necrotic tissue or slough.

Prior to administering the collagen and a gelatin-reducing agent to the wound (either separately, together as a mixture, or together in the form of a wound dressing), the wound may be pretreated, such as by cleaning or debriding the wound. Open wounds may be infected and/or may include foreign materials that may lead to infection or delay wound healing. In particular, pretreatment may be carried out to remove foreign materials or infectious agents in or around the wound. Debridement may be carried out to loosen and remove necrotic, infected, or other damaged tissue in the wound in order to promote healing.

The method for cleaning or debriding the wound is not particularly limited. Conventional wound cleaning or debriding treatments may be used, as needed, such as curettage or sharp debridement. Some debridement techniques may encourage autolytic (e.g., enzymatic) debridement, such as by applying occlusive materials to the wound (e.g., a medical grade polysaccharide such as honey). Collagenase enzyme is itself sometimes used to promote debridement, but application of collagenase may not be suitable within a certain amount of time before applying the wound treatment provided herein because the collagen in the wound treatment may engage the collagenase used for debridement. Therefore, the collagenase would not be fulfilling the primary purpose for using it, namely to remove necrotic collagenous tissue. Also, if one first uses externally supplied collagenase to remove necrotic tissue to prepare the wound bed for a collagen dressing, and then later uses the collagen dressing, this sequential treatment has lengthened the total time needed to achieve improved wound healing. Collagenase, supplied externally for debridement purposes, is also rendered ineffective with silver ions, which are frequently present in the wound from silver-containing wound dressings.

In at least one approach, the method for promoting wound healing comprises administering a wound treatment comprising collagen and a gelatin-reducing agent to a wound of a subject in need of wound healing. The wound treatment is delivered to the wound in a therapeutically effective amount to promote wound healing. While the collagen and gelatin-reducing agent may be delivered to the wound together or in short succession (such as within five minutes), it is also contemplated that the collagen and gelatin-reducing agent may be administered sequentially, preferably so that one is administered within about 30 minutes of the other. This "parallel" mode of treatment allows for the gelatin-reducing agent and collagen to provide for faster wound healing by removing necrotic tissue removal and promoting wound healing at the same time.

The method may further comprise covering the treated wound with a conventional wound dressing, gauze, or bandage, if desired. The method may further comprise preparing the wound treatment by mixing collagen and a gelatin-reducing agent with a pharmaceutically acceptable carrier prior to administering the wound treatment to the subject. If provided in powder or other solid form, the wound treatment may be hydrated prior to use, such as by addition of physiologically acceptable fluid to the wound treatment. In other approaches, the wound treatment may be applied to the site of the wound in powder form, such that biological fluid at the site of the wound is sufficient to solubilize the composition.

The wound treatment may be administered to the wound in any desirable route, such as by topical administration or by irrigating the wound with the composition. Administration may also be carried out by spraying, pouring, inserting (such as via a syringe), injecting, or dropping (such as with a medicine dropper or pipette) the wound treatment onto the wound.

In the methods described herein, the wound treatment is delivered in an effective amount to a damaged tissue in a subject in need of treatment. As used herein, the term "subject" includes mammals, such as but not limited to rodents, pigs, cats, dogs, and primates, and specifically includes humans. The term "effective amount" or "therapeutically effective amount" means the amount that will elicit the biological or medical response of a subject that is being sought by a medical doctor or other clinician. In one aspect, the term "effective amount" is intended to mean the amount that will bring about a biologically meaningful improvement in the wound.

Data obtained from animal studies can be used in formulating a range of dosages for human use. The dosage may vary depending upon the dosage form employed, sensitivity of the patient, and the route of administration. The dosage suitable for a given subject can be determined by one of skill in the art. Generally, dosage and administration can be adjusted to provide or to maintain the desired effect. The optimal dose of collagen and gelatin-reducing agent may depend, at least in part, on the severity of the wound and method of delivery.

The treatment regimen can vary depending on the particular needs of the subject. For example, the dose and frequency of administration may depend in part on the size or severity of the wound. By way of non-limiting illustration, the wound treatment may be applied at least once daily. Some subjects may benefit from more frequent application of the composition. In one approach, the collagen may be applied from daily to weekly, and the gelatin-reducing agent may be applied from daily to about once every three days.

It is thus seen that a wound treatment may be provided and used in accordance with the foregoing teachings.

As used herein, all percentages are by weight unless stated otherwise.

All methods described herein can be performed in any suitable order unless otherwise indicated herein or otherwise clearly contradicted by context. The use of any and all examples, or language describing an example (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A surface wound treatment composition comprising, in combination, collagen and a poloxamer, the collagen and the poloxamer being present in a weight ratio with respect to one another ranging from 35:65 to 65:35 collagen:poloxamer, wherein the treatment composition is in powder form.

2. The surface wound treatment composition according to claim 1, wherein at least a majority of the collagen is native collagen.

3. The surface wound treatment composition according to claim 1 wherein the poloxamer comprises one or more of poloxamer 101, poloxamer 105, poloxamer 105 benzoate, poloxamer 108, poloxamer 122, poloxamer 123, poloxamer 124, poloxamer 181, poloxamer 182, poloxamer 182 dibenzoate, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403 or poloxamer 407.

4. The surface wound treatment composition according to claim 1, wherein the poloxamer comprises poloxamer 188.

5. A wound dressing comprising:
a substrate having a wound contacting layer;
collagen; and
a poloxamer;
the collagen and the poloxamer being present in a weight ratio with respect to one another ranging from 35:65 to 65:35 poloxamer,
the collagen being present in said dressing in an amount effective to reduce wound collagenase activity, and the poloxamer being present in an amount effective to reduce wound gelatin formation,
wherein the collagen and poloxamer are in powder form.

6. The wound dressing according to claim 5, wherein at least a majority of the collagen is native collagen.

7. The wound dressing according to claim 5, wherein the poloxamer comprises one or more of poloxamer 101, poloxamer 105, poloxamer 105 benzoate, poloxamer 108, poloxamer 122, poloxamer 123, poloxamer 124, poloxamer 181, poloxamer 182, poloxamer 182 dibenzoate, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403 or poloxamer 407.

8. The wound dressing according to claim 5, wherein the poloxamer comprises poloxamer 188.

9. A method for promoting wound healing in a subject, the method comprising administering collagen and a poloxamer to a surface wound, the collagen being administered in an amount effective to reduce wound collagenase activity, and the poloxamer being administered in an amount effective to reduce wound gelatin formation;
the poloxamer and the collagen being administered to the surface wound in a weight ratio with respect to one another ranging from 35:65 to 65:35 collagen:poloxamer,
wherein the collagen and poloxamer are administered to the surface wound in powder form.

10. The method according to claim 9, wherein the collagen and the poloxamer are administered sequentially.

11. The method according to claim 9, wherein the collagen and the poloxamer are administered together as a mixture.

12. The method according to claim 9, wherein the collagen and the poloxamer are administered to the wound as part of a dressing comprising a substrate having a wound contacting layer; the collagen; and the poloxamer; the collagen being present in said dressing in an amount effective to reduce wound collagenase activity, and the poloxamer being present in an amount effective to reduce wound gelatin formation.

13. The method according to claim 9, wherein at least a majority of the collagen is native collagen.

14. The method according to claim 9, wherein the poloxamer comprises one or more of poloxamer 101, poloxamer 105, poloxamer 105 benzoate, poloxamer 108, poloxamer 122, poloxamer 123, poloxamer 124, poloxamer 181, poloxamer 182, poloxamer 182 dibenzoate, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403 or poloxamer 407.

15. The method according to claim 9, wherein the poloxamer comprises poloxamer 188.

16. The surface wound treatment composition according to claim 1, wherein all of the collagen is native collagen.

17. The wound dressing according to claim 5, wherein all of the collagen is native collagen.

18. The method according to claim 9, wherein all of the collagen is native collagen.

19. A wound dressing comprising:
a substrate having a wound contacting layer;
collagen; and
a poloxamer;
the collagen and the poloxamer being present in a weight ratio with respect to one another ranging from 35:65 to 65:35 poloxamer,
the collagen being present in said dressing in an amount effective to reduce wound collagenase activity, and the poloxamer being present in an amount effective to reduce wound gelatin formation,
wherein the collagen and the poloxamer are in the form of a liquid solution or suspension.

20. The wound dressing according to claim 19, wherein at least a majority of the collagen is native collagen.

21. The wound dressing according to claim 19, wherein the poloxamer comprises one or more of poloxamer 101, poloxamer 105, poloxamer 105 benzoate, poloxamer 108, poloxamer 122, poloxamer 123, poloxamer 124, poloxamer 181, poloxamer 182, poloxamer 182 dibenzoate, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403 or poloxamer 407.

22. The wound dressing according to claim 19, wherein the poloxamer comprises poloxamer 188.

23. The wound dressing according to claim 19, wherein all of the collagen is native collagen.

24. A method for promoting wound healing in a subject, the method comprising administering collagen and a poloxamer to a surface wound, the collagen being administered in an amount effective to reduce wound collagenase activity, and the poloxamer being administered in an amount effective to reduce wound gelatin formation;

the poloxamer and the collagen being administered to the surface wound in a weight ratio with respect to one another ranging from 35:65 to 65:35 collagen:poloxamer, wherein the collagen and poloxamer are administered to the surface wound in the form of a liquid solution or suspension.

25. The method according to claim 24, wherein the collagen and the poloxamer are administered sequentially.

26. The method according to claim 24, wherein the collagen and the poloxamer are administered together as a mixture.

27. The method according to claim 24, wherein the collagen and the poloxamer are administered to the wound as part of a dressing comprising a substrate having a wound contacting layer; the collagen; and the poloxamer; the collagen being present in said dressing in an amount effective to reduce wound collagenase activity, and the poloxamer being present in an amount effective to reduce wound gelatin formation.

28. The method according to claim 24, wherein at least a majority of the collagen is native collagen.

29. The method according to claim 24, wherein the poloxamer comprises one or more of poloxamer 101, poloxamer 105, poloxamer 105 benzoate, poloxamer 108, poloxamer 122, poloxamer 123, poloxamer 124, poloxamer 181, poloxamer 182, poloxamer 182 dibenzoate, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403 or poloxamer 407.

30. The method according to claim 24, wherein the poloxamer comprises poloxamer 188.

31. The method according to claim 24, wherein all of the collagen is native collagen.

* * * * *